United States Patent [19]
Heinzen et al.

[11] Patent Number: 6,053,889
[45] Date of Patent: *Apr. 25, 2000

[54] SAMPLE DELIVERY MODULE FOR PARTICLE ACCELERATION APPARATUS

[75] Inventors: Richard J. Heinzen, North Freedom; Dennis E. McCabe, Middleton, both of Wis.

[73] Assignee: PowderJect Vaccines, Inc., Madison, Wis.

[ * ] Notice: This patent is subject to a terminal disclaimer.

[21] Appl. No.: 08/874,784

[22] Filed: Jun. 13, 1997

Related U.S. Application Data

[63] Continuation-in-part of application No. 08/665,116, Jun. 14, 1996.

[51] Int. Cl.⁷ .................................................. A61M 5/30
[52] U.S. Cl. ................................................. 604/68; 604/24
[58] Field of Search ........................ 604/23, 24, 57–62, 604/68–72, 131, 140, 146, 147, 151

[56] References Cited

U.S. PATENT DOCUMENTS

| | | |
|---|---|---|
| 2,754,818 | 7/1956 | Scherer . |
| 5,062,830 | 11/1991 | Dunlap . |
| 5,149,655 | 9/1992 | McCabe et al. . |
| 5,549,560 | 8/1996 | Van de Wijdeven . |
| 5,584,807 | 12/1996 | McCabe . |
| 5,630,796 | 5/1997 | Bellhouse et al. . |

FOREIGN PATENT DOCUMENTS

| | | |
|---|---|---|
| 4239402 A1 | 11/1992 | Germany . |
| WO 92/04439 | 3/1992 | WIPO . |
| WO 92/05823 | 4/1992 | WIPO . |
| WO 95/19799 | 7/1995 | WIPO . |
| WO 96/04947 | 2/1996 | WIPO . |

*Primary Examiner*—Wynn Wood Coggins
*Assistant Examiner*—Deborah Blyveis
*Attorney, Agent, or Firm*—Thomas P. McCracken

[57] ABSTRACT

A sample delivery module for use in conjunction with a particle acceleration apparatus includes a fitting for connecting the sample delivery module to the apparatus. The sample delivery module provides a particle acceleration path which includes a portion adapted to receive a sample of particles coated with a biological material, a particle acceleration chamber coaxial with, and in fluid communication, with the cartridge chamber, and a substantially conical exit nozzle coaxial with and in fluid communication with the particle acceleration chamber. In use, a gas stream causes sample particles to be entrained therein and accelerated through the particle acceleration chamber and the exit nozzle toward a target.

17 Claims, 4 Drawing Sheets

FIG. 8 ly acceler-
SAMPLE DELIVERY MODULE FOR PARTICLE ACCELERATION APPARATUS

CROSS-REFERENCE TO RELATED APPLICATION

This application is a continuation-in-part of U.S. application Ser. No. 08/665,116, filed Jun. 14, 1996, from which priority is claimed pursuant to 35 U.S.C. §120 and which is incorporated herein by reference in its entirety.

TECHNICAL FIELD

The present invention relates to the field of delivering biological material into cells, more particularly to delivering biological material into cells using particle-mediated delivery techniques.

BACKGROUND OF THE INVENTION

Particle-mediated delivery of biological material, particularly genetic material, into living cells and tissue has emerged as an important tool of plant and animal biotechnology. Transient and long-term expression of introduced genetic material from target cells, as well as successful integration of introduced DNA into germ cells, have been demonstrated in a wide variety of microorganisms, plants, and animals.

One limitation of existing particle-mediated delivery devices is the form in which the biological sample must be provided. In such prior devices, the biological sample is coated onto the surface of small, dense carrier particles comprised of a dense material such as gold or platinum. The coated particles are themselves arranged on a carrier surface, such as a rigid surface or metal plate, or a planar carrier sheet made of a fragile material such as mylar. The carrier surface is then accelerated toward a target, and the coated carrier particles are dislodged from the surface thereof for delivery to a target. This approach has several advantages as well as some disadvantages. One advantage provided by the use of a carrier surface, such as a planar sheet, is that a very uniform spread of accelerated particles can be delivered into a target surface. One disadvantage is that each carrier surface must be prepared individually and used only once, making use of such devices time-consuming and inefficient. This is particularly problematic when repetitive delivery must be carried out. Each coated carrier surface is also relatively large and must be handled with care to avoid damage or contamination during loading of a particle acceleration device. It may also be difficult to distinguish the coated side of a carrier surface from the uncoated side, which increases the possibility of improper positioning of the carrier surface in an acceleration device. Such improper positioning can reduce throughput and result in substantial waste of biological samples.

The distribution or spread of carrier particles delivered from a particle acceleration apparatus can be critical in some applications, particularly when the biological material being delivered is comprised of genetic material. For example, in applications where germline transformation events are desired, the need to control the delivery pattern of carrier particles is substantially more acute than in other applications, such as where only transient expression of introduced genetic material is needed. When an infrequent germline transformation event is desired, it is necessary to uniformly accelerate the carrier particles toward a large target area to increase the likelihood that one or more target cells will be transformed. Thus, one approach to such transformations has been to distribute the coated carrier particles as a monolayer on a relatively large carrier surface. This helps maximize the number of cells receiving particles under precisely uniform conditions. In applications where coated particles are accelerated into cells to induce transient gene expression in somatic tissues such as skin, there is a less compelling need to provide a uniform particle distribution, since adequate expression can be accomplished even when a relatively low number of cells receive the particles.

In particle acceleration applications wherein coated particles are used to deliver nucleic acid vaccines preparations, genetic material encoding an antigenic determinant is delivered into a target tissue. In those cells that have been successfully transfected with the genetic material, transient expression of a protein or peptide encoded by the genetic material ensues, eliciting an immune response against the protein or peptide. These and other therapeutic or medicinal applications of particle acceleration technologies present practical considerations such as the need to maintain the cleanliness and, possibly, the sterility of an apparatus used to deliver the particles to a recipient. These issues take on particular significance when the apparatus is to be used in large-scale immunization projects. For these and other reasons, then, the art has a particular need for a particle acceleration apparatus that can be used without contaminating samples or targets, as well as an apparatus that avoids inappropriate delivery of residual particles trapped in the particle delivery path.

SUMMARY OF THE INVENTION

The present invention provides a sample delivery module for use with a particle acceleration apparatus. The module can be used to deliver a biological sample, for example, nucleic acids such as DNA or RNA molecules, peptides, or proteins, to a target cell.

Accordingly, in one embodiment, the subject invention is directed to a sample delivery module for use in a particle acceleration apparatus. The module comprises, in operative combination, (i) a cartridge chamber configured to accept and retain a particle cartridge, wherein the chamber has an upstream terminus and a downstream terminus; (ii) an exit nozzle having an upstream terminus and a downstream terminus; (iii) a particle acceleration passage arranged between the cartridge chamber and the exit nozzle, wherein the acceleration passage is in fluid communication with the downstream terminus of the cartridge chamber and the upstream terminus of the exit nozzle; and (iv) securing means for coupling the sample delivery module to a source of motive force, wherein the securing means interfaces the upstream terminus of the cartridge chamber with an associated source of motive force.

In related aspects of the present invention, the sample delivery module is configured such that the exit nozzle has a conical geometry, and, in a preferred embodiment, the downstream terminus of the exit nozzle has a greater diameter than the upstream terminus thereof, and the distance between the upstream and downstream termini of the exit nozzle is greater than the diameter of the downstream terminus.

It is an advantage of the present invention that the sample delivery module is independent from an associated motive force-generating portion of an acceleration apparatus, and that the module can be adapted either for a single particle delivery operation, wherein the module is disposable, or for multiple uses, wherein the module can be cleaned between uses. The use of a disposable sample module eliminates the possibility of sample cross-contamination between subsequent deliveries from an acceleration apparatus.

It is also an advantage of the present invention that the sample delivery module can comprise a securing means that provides a positive, pressure-tight coupling between the module and an associated source of motive force, and that samples can be prepared in advance of use and thus stored and handled with ease.

In another embodiment, the invention is drawn to a particle acceleration apparatus, comprising: (a) an instrument body comprising a conduit extending therethrough and having a first terminus adapted for coupling to a source of compressed gas and a second terminus adapted for coupling to a sample delivery module, wherein the instrument body further includes actuation means for releasing a flow of gas through the conduit; and (b) a sample delivery module having (i) a cartridge chamber configured to accept and retain a particle cartridge, wherein the chamber has an upstream terminus and a downstream terminus; (ii) an exit nozzle having an upstream terminus and a downstream terminus; (iii) a particle acceleration passage arranged between the cartridge chamber and the exit nozzle, wherein the acceleration passage is in fluid communication with the downstream terminus of the cartridge chamber and the upstream terminus of the exit nozzle; and (iv) securing means for coupling the sample delivery module to the instrument body, wherein the securing means interfaces the upstream terminus of the cartridge chamber with the second terminus of the instrument body conduit.

In related aspects of the present invention, the particle acceleration apparatus includes an actuation means comprised of a valve or rupturable membrane and arranged in the instrument body between the first and second terminus of the conduit to control the passage of gas therethrough.

Other objects, features and advantages of the present invention will become apparent from the following specification, read in light of the accompanying drawings.

DETAILED DESCRIPTION OF THE PREFERRED EMBODIMENT

Before describing the present invention in detail, it is to be understood that this invention is not limited to particular particle delivery devices or to particular carrier particles as such may, of course, vary. It is also understood that different embodiments of the disclosed sample delivery modules and related devices may be tailored to the specific needs in the art. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a", "an", and "the" include plural referents unless the content clearly dictates otherwise. Thus, for example, reference to "a coated particle" includes reference to mixtures of two or more such particles, and the like.

The present invention provides a sample delivery module for use in a particle acceleration apparatus. The sample delivery module allows for reproducible, sequential delivery of particles coated with a biological material, such as genetic material, into a recipient cell or target tissue. The module is self-contained, and is connectable to a portion of a particle acceleration instrument that generates a motive force sufficient for delivering the coated particles toward and into a target. In particular embodiments, the sample delivery module is configured to allow rapid coupling and decoupling thereof with an associated source of motive force. Further, the delivery module can be a disposable, single-use device.

In preferred embodiments of the invention, the sample delivery module is formed or molded from an inexpensive polymeric material, such as a thermoplastic resin, making it economically feasible to dispose of the sample delivery module after a single use. Alternatively, the sample delivery module can be comprised of a more resilient and reusable material, such as those materials that can withstand cleaning processes sufficient to remove and/or destroy residual biological materials. For example, the sample delivery module can be comprised of a material that can withstand common sterilization processes. Suitable materials include polycarbonates or polypropylenes commonly used in the construction of medical grade devices or instruments.

For use in a clinical setting, it is preferred that the sample delivery module be provided in a sealed, sterile container of a type commonly used to store single use medical device parts, such as disposable syringes.

Figure 1:
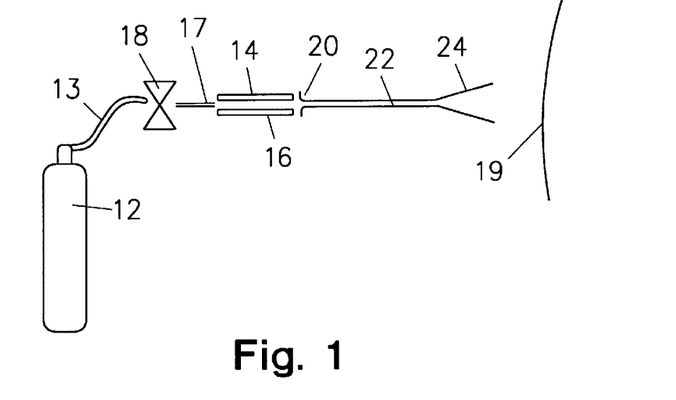
FIG. 1 is a schematic depiction of a particle acceleration apparatus in accordance with the present invention.

FIG. 1 depicts a schematic illustration that is intended to illustrate the general method of operation of a particle acceleration instrument incorporating the present invention. The components of the apparatus illustrated in FIG. 1 are shown in slightly exploded view in some places for purposes of clarity. This particular illustration is intended to illustrate the basic operating principle of a particle acceleration apparatus, rather than illustrate construction details.

Referring to the apparatus depicted in FIG. 1, a carrier particle cartridge 14 is located in the instrument. The particle cartridge 14 is an elongate concave or tubular structure that has a concave hollow passage passing through its center. A plurality of carrier particles 16 are disposed on the interior of the cartridge. The carrier particles, as will be discussed in further detail below, are small, dense particles which have been previously coated with a biological material, e.g., DNA or RNA, that is intended to be delivered into a target cell or tissue. The carrier particles may alternatively be coated with other types of biological materials such as peptides, cytokines, hormones, or proteins. An actuator 18, for example a gas valve or rupturable membrane, is located upstream of the carrier particle cartridge and is in fluid communication with the interior of the carrier particle cartridge 14 via an appropriate conduit 17. The actuator is connected, by appropriate tubing generally indicated at 13, with a source of compressed gas 12. The source of compressed gas 12 can be a conventional commercial compressed gas tank, preferably of an inert compressed gas such as helium. A reservoir of compressed gas is generally desirable between the gas source 12 and the actuator 18; however, the tubing 13 can function as such a reservoir.

Adjacent to the carrier particle cartridge is an orifice 20 which provides fluid communication with the interior of an acceleration chamber 22 which communicates, in turn, with a conical exit nozzle 24. The target, e.g., a patient, tissue, or cell, is designated as 19 in the Figure.

In general operation of the device of FIG. 1, the actuator 18 is used to release a pulse of compressed gas held in the reservoir formed by the tubing 13. A particle acceleration passage disposed between the actuator 18 and the exit nozzle 24, provides a path through which the released gas creates a gas stream traveling at significant speed. The gas stream accelerates through the particle acceleration passage and, as it passes through the interior of the particle cartridge 14, dislodges the carrier particles 16. The accelerating gas stream, containing the dislodged particles, passes through the chamber 22 and into the exit nozzle 24. In this manner, the carrier particles are delivered from the instrument and into the target 19, where the carrier particles lodge into, but do not kill, the cells of the target or patient.

Figure 2A:
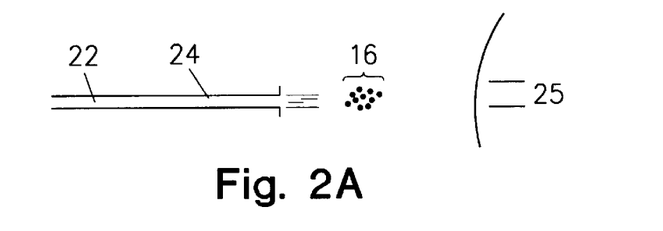
FIG. 2 is a schematic illustration showing the effects of varying the angle of the exit nozzle.
Figure 2B:
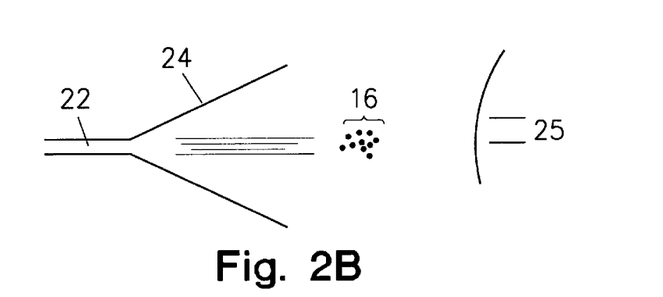
Figure 2C:
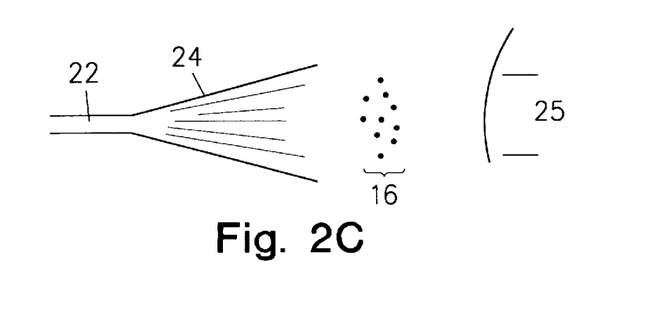

One particularly important feature of the device of FIG. 1 is the geometry of the exit nozzle 24. Referring now to FIG. 2, three different possible geometries of the exit nozzle 24 are illustrated schematically as Versions A, B, and C. Also depicted is the effect of these different exit nozzle geometries upon the delivery pattern of the carrier particles 16. In Version A, the exit nozzle 24 does not widen significantly toward the downstream end thereof. Thus, the exiting gas stream passes substantially linearly from the exit nozzle 24, and proceeds directly toward the target. As a result, the carrier particles continue in a relatively linear path and provide a focused delivery pattern that impacts a relatively narrow area 25 of the target. While the particles 16 diverge somewhat from their linear flight, the divergence is quite small and insignificant.

Similarly, in Version B of FIG. 2, the exit nozzle 24 has an exceedingly wide angle of conical taper toward the downstream terminus thereof. In this configuration, the gas stream exits the instrument fairly linearly, and the carrier particles 16 do not disperse widely. Again, the particles impact a relatively compact portion 25 of the target.

A substantially different delivery pattern is obtained; however, when the angle of taper of the conical exit nozzle is less than a critical angle. This phenomenon is illustrated as Version C in FIG. 2. In particular, as the accelerated gas stream passes into the exit nozzle, it creates, through a vortex action, a vacuum between the route of passage of the gas stream and the sides of the exit nozzle 24. This vacuum causes the gas stream to be pulled outwardly in all directions perpendicular to the direction of travel of the gas stream. In this manner, the gas stream and the particles entrained within the gas stream are dispersed in a direction lateral to the major axis of the exit nozzle (i.e., the direction of travel of the particles). Thus, as can be seen in Version C of FIG. 2, the gas stream passing out of the instrument is spread laterally over a wider area, thereby distributing the carrier particles 16 over a wider area and providing an improved delivery profile over a much wider area 25 of the target than would be the case if the conical exit nozzle were not so shaped. This avoids overdosing any one small area of the target with carrier particles, and provides a relatively broad and even distribution of the carrier particles without the need for mechanical distribution of the particles or elaborate gas diverting or distributing equipment.

The exact angle of taper of the conical exit nozzle 24 will vary from embodiment to embodiment depending on gas pressure used and the size of the acceleration chamber 22. For an instrument which uses a commercial helium tank as the source of motive force, wherein the acceleration chamber 22 has a diameter of approximately $1/16$ inch, an exit nozzle which tapers from $1/16$ inch to $2/3$ of an inch over a span of 3.3 inches will provide a satisfactory particle distribution pattern which covers a target surface having a diameter of from about $1/16$ inch to about $2/3$ of an inch. This represents over a 100-fold increase in the particle distribution pattern, with a concomitant 100-fold decrease in the particle distribution density.

Thus, in preferred embodiments, the conical exit nozzle 24 must be significantly longer along its major axis (e.g. 3.3 inches) than it is wide at either of its upstream or downstream termini (e.g. $1/16$ to $2/3$ inch). A nozzle having a conical taper that has a diameter that is greater than its length will not provide a proper dispersion of carrier particles for the purposes of the invention. However, it is not necessary that the conical exit nozzle have a continuously conical interior geometry. For example, the exit nozzle can have several small stepped increases in diameter, rather than a continuous increase in diameter, without adversely affecting its overall function.

By varying the pressure of the gas, the force with which particles impact the target 19 may be varied. In the practice of the invention, the gas pressure provided by the source of motive force must be sufficient to dislodge the coated particles 16 from the cartridge 14, but not so great as to damage the target 19. When delivering coated particles into intact animal skin, it has been found that a discharged gas stream will not harm the targeted skin surface. At some gas higher pressures, some minor reddening of the skin occurs at very tolerable levels. A regulated gas pressure, such as that available from commercially available compressed helium tanks, has been found to be satisfactory for detaching the carrier particles 16 and delivering the same into epidermal cells of a target animal without untoward damage to the target skin or cells. Lower pressures or higher pressures may work in particular applications, depending upon the density of the carrier particles, the nature of the target surface, and the desired depth of particle penetration. Delivery parameters associated with delivery of carrier particles into pig skin is analogous to that expected with human skin, due to the mechanical similarity between human and porcine skin.

The particle cartridge 14 can be formed from a concave structure, preferably a tubular structure, and has particles deposited on its inner surface. Such particle cartridges can be readily handled without contacting the carrier particles, thus maintaining the integrity and, possibly, the sterility of the sample. While many shapes and geometries of the particle cartridge 14 are possible under the invention, a simple and functional version can be provided using a short segment of tubing comprised of a substantially inert polymeric material such as poly(ethylenetetra-fluoroethylene), available under the tradename of Tefzel®. The tubing forms a cylinder with a passage through its center. An advantage of such a tubular structure is that the carrier particles, coated with a biological material, are disposed on the interior surface of the tubing and thus do not contact and, possibly contaminate, the walls of the delivery apparatus. An advantage of using a material such as Tefzel® is that it is transparent, allowing loaded cartridges to be visually identified. Such identification is by the appearance of the cartridge which will, for example, be visibly tinged gold, or have a visible stripe of gold when gold carrier particles are being used. The inner diameter of the cartridge need only be large enough to allow particles to be deposited therein, and to allow adequate gas flow therethrough at a pressure sufficient to dislodge the particles. The cartridge 14 does not need to be tubular; however, and can be configured as any suitable concave shape in which the pressurized gas can be confined. Such alternative geometries ensure that the dislodged particles 16 are not dispersed, and thus directed toward the target by the gas stream. By way of example, the cartridge 14 can be comprised of a half-tube in which carrier particles 16 are deposited. The half-tube can then be covered tightly by a planar or non-planar surface of the apparatus to form a half-cylindrical path through which the gas can pass. In this regard, the particular geometries of the sample cartridge and the surrounding chamber formed by a surface of the apparatus are not critical, as long as together, the geometries direct gas flow from the cartridge 14 to the target 19.

Suitable carrier particles 16 for use in the sample cartridge 14 can be comprised of any high density, biologically inert material. Dense materials are preferred in order to provide particles that can be readily accelerated toward a target over a short distance, wherein the particles are still sufficiently small in size relative to the cells into which they are to be delivered. It has been found that carrier particles having an average diameter of a few microns can readily enter living cells without unduly injuring such cells.

For the purposes of the invention, tungsten, gold, platinum and iridium carrier particles can be used. Tungsten and gold particles are preferred. Tungsten particles are readily available in average sizes of 0.5 to 2.0 $\mu$m in diameter, and are thus suited for intracellular delivery. Although such particles have optimal density for use in particle acceleration delivery methods, and allow highly efficient coating with nucleic acids, tungsten may potentially be toxic to certain cell types. Thus, gold is a preferred material for the carrier particles 16, since gold has high density, is relatively inert to biological materials and resists oxidation, and is readily available in the form of spheres having an average diameter of from about 0.2 to 3 $\mu$m. Spherical gold particles, or beads, in a size range of 1–3 microns have been successfully used in particle acceleration delivery technologies, as well as gold provided in the form of a microcrystalline powder having a measured size range of about 0.2 to 3 $\mu$m.

Figure 8:
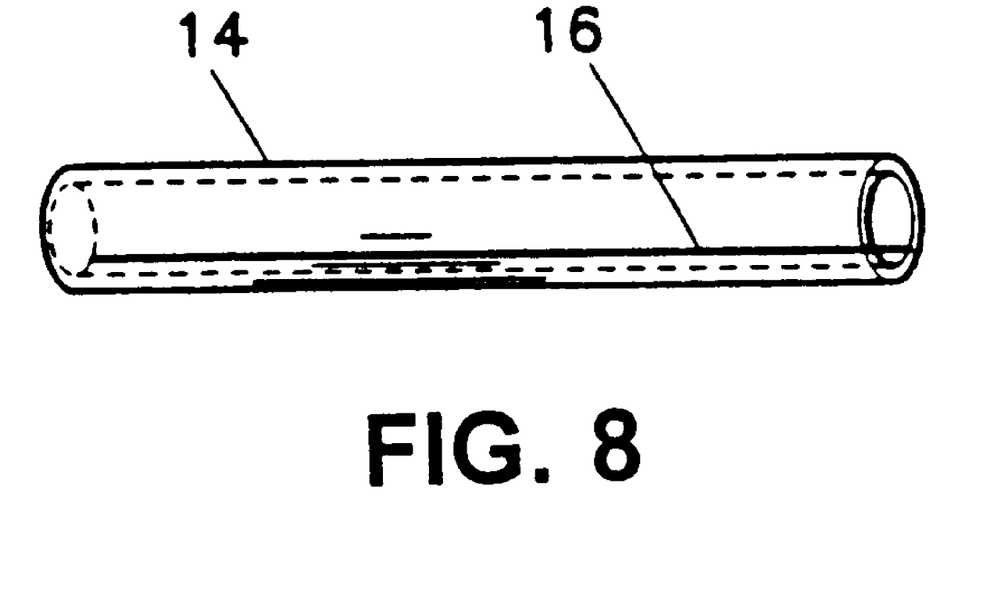
FIG. 8 is a side, cutaway view of a tubular sample cartridge for use in the exemplified embodiment.

A large number of sample cartridges 14, such as the tubular structure of FIG. 8, which have carrier particles 16 adhered thereto, can be prepared in a single procedure. In this regard, two different application methods have been successfully used.

In a first method, a suspension of carrier particles coated with a biological material of interest is introduced into a length of plastic tubing, The particles are allowed to settle under the force of gravity along the bottom of the inner surface of the tubing. Upon settling, the particles form a ribbon of particles along the full length of the tubing, and liquid from the particle suspension can be drained from the tubing. As the liquid is removed, the tubing is rolled in order to spread the particles over the entire inner surface of the tubing, and the distributed particles are dried under a stream of a drying gas such as nitrogen. The tubing can then be cut into lengths appropriate for insertion into a sample chamber of a particle delivery apparatus. One of ordinary skill will recognize that the number of coated particles available for transfer may be varied by adjusting the concentration of the particle suspension, or by adjusting the length of tubing used to form a cartridge. One will also recognize that sample cartridges useful in the present invention may be prepared in ways other than that just described.

A second method for coating the inner surface of a tubular structure uses a slight adhesive effect to secure the carrier particles 16 to the particle cartridge 14. It has been found that the use of a slight adhesive helps ensure that the particles are accelerated well by keeping them adhered temporarily to the interior concave surface of the cartridge until the gas stream achieves an adequate delivery pressure. To accomplish this, an additive is used when the particles are suspended in alcohol. Additives which are only slightly adhesive and which have been used with success are polyvinyl pyrrolidone (PVP), cholesterol, glycerin and water. Cholesterol, for example, is used at a rate of 1 mg cholesterol per ml of alcohol in the suspension. The particle/alcohol suspension is sonicated, to help maintain the particles in suspension, and the suspension is applied to the interior surface of the cartridge 14 which is placed on its side. The carrier particles rapidly fall out of suspension along one side of the interior surface of the cartridge. The alcohol can then be removed, and the interior of the cartridge dried with a nitrogen stream as the tube is rotated.

Figure 3:
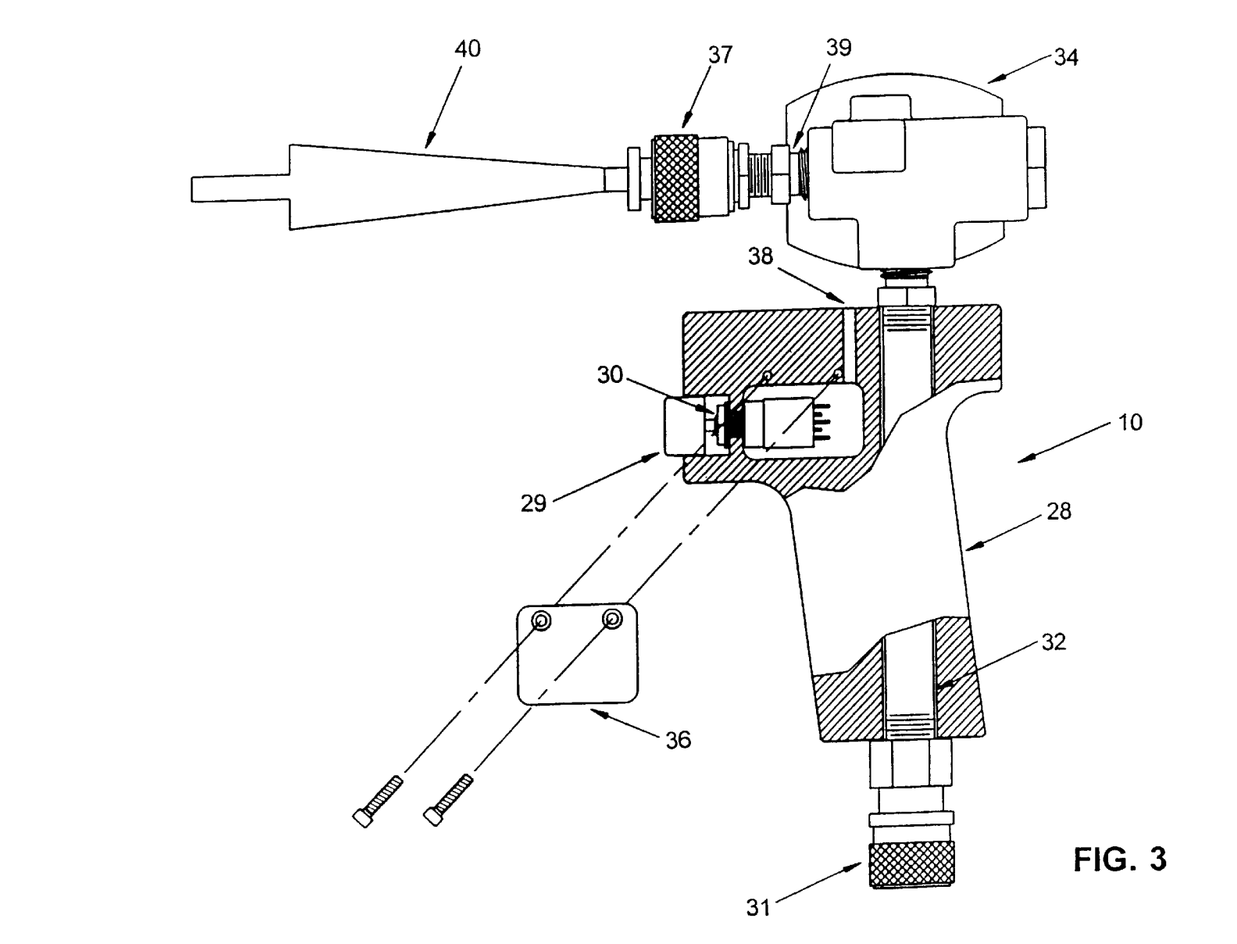
FIG. 3 is a side view of a particle acceleration apparatus comprising the improved delivery portion of the present invention.

Referring now to FIG. 3, a side view of an embodiment of a particle acceleration apparatus, generally indicated at 10, is shown with an installed disposable sample delivery module constructed in accordance with the present invention. The apparatus 10 is hand-manipulable and portable, allowing it to be readily handled and moved by an operator.

Turning to the details of the apparatus of FIG. 3, the motive force-generating portion of the device includes a handle 28 that is preferably elongate and can be of any suitable shape or size adapted to the needs and comfort of a particular operator. As shown in FIG. 3, the handle 28 can be formed in the shape of a pistol grip to provide the operator with a firm grip and ready access to an actuator 30, e.g., a valve trigger mechanism, that can be covered by a cap 29 that engages the actuator mechanism 30 when pressed by an operator.

An inlet tube 32, or conduit, passes through the handle 28, wherein the inlet tube is open at both ends and comprised of a solid material that can contain gas at pressures needed to deliver particles from the apparatus. In preferred embodiments, the inlet tube 32, and all other portions of the apparatus (other than the sample cartridge) that contact the pressurized gas stream are comprised of a non-deformable solid material, such as metal, e.g., brass, or a high density polymeric material. The inlet tube 32 can be secured in place in the instrument by bushings or the like. The inlet tube 32 acts as a reservoir which provides a releasable volume of gas under sufficient operating pressure to accomplish a particle-accelerated delivery. The dimensions of the inlet tube 32 are not critical, and may be increased or decreased to accommodate a sufficient volume of gas under pressure. Alternatively, a separate dedicated gas reservoir can be provided if the volume within the inlet tube 32 is insufficient.

At one terminus of the inlet tube 32 is a coupler 31 that is connectable through flexible tubing to an external gas source, generally indicated at 12. The connector 31 is preferably a quick-connect type connector of a type commonly used in pneumatic devices employing gases at elevated pressures. The gas source can be a commercial tank containing a biologically and chemically inert compressed gas. The inert gas is preferably helium. The pressure at which gas leaves the gas source is advantageously regulated by a conventional pressure regulator valve. A gauge visible to the operator can be used to display the pressure in the device.

An actuator means, 34, such as a valve or rupturable membrane, is connected to the opposite terminus of the inlet tube 32. The actuator means is used to control the flow of gas from the inlet tube 32 to the sample delivery portion of the apparatus 10. In the embodiment of FIG. 3, the actuator 34 is an electrically-actuated solenoid valve that is controlled by a trigger mechanism 30 on the handle 28. Wires which connect the solenoid valve with the trigger mechanism can be disposed within the handle 28 to improve the safety and manageability of the apparatus. A removably securable cover plate 36 provides access to internal electrical connections with the trigger mechanism 30. A wiring channel 38, which passes through the handle 23, provides a protected conduit for wires that interconnect the trigger mechanism 30 and the actuator 34.

The invention is not limited to the particular type of actuator valve, nor to any particular trigger mechanism. In this regard, many valve and trigger combinations are known that may be substituted by one of ordinary skill for the combination depicted in FIG. 3. Spring-loaded ball valves can be used, as well as actuator mechanisms that operate by rupture or breakage of a frangible closing to release a restricted flow of pressurized gas. Such combinations are suitable for use herein as long as the actuator mechanism can withstand the pressure of the gas stream entering from the inlet tube 32.

The fluid outlet of the actuator 34 includes a gas outlet tube 39 which is coupled to the valve and a terminal connector 37 adapted to receive the sample delivery module (generally indicated at 40) of the present invention. To facilitate easy and repetitive attachment and removal of the sample delivery module 40, the connector 37 can be a quick-connect coupler of the type referred to above.

Figure 4:
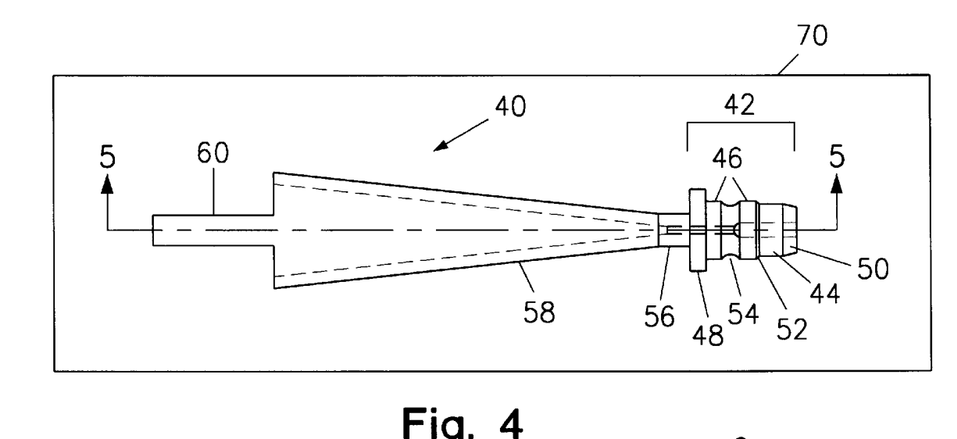
FIG. 4 is a side view of an embodiment of the improved delivery portion of the present invention.

The present invention resides, in part, in the sample delivery module 40, and in part in the use thereof with a particle acceleration apparatus 10 that is capable of providing a suitable motive force. The sample delivery module 40 includes the elements necessary to deliver a sample to a target when connected to the motive force-generating portion of the instrument 10. The sample delivery module 40 is described in more detail with reference to FIGS. 4–7. As depicted in FIG. 4, one particular embodiment of the invention includes a securing means 42 for rapidly connecting the sample delivery module to the connector 37. In this embodiment, the securing means 42 comprises an end fitting that is adapted in size and shape to securely engage the connector 37. The particular size and shape of the securing end-fitting is not crucial, as long as it corresponds to that of the connector 37 in such a way that the sample delivery module can be firmly coupled to the source of motive force during use. In this regard, it is preferable that the securing means is engagable and detachable in a matter of seconds.

The end fitting of the securing means 42 is depicted in FIG. 4 as the type of quick connect connector commonly referred to as a "swagelok" quick-connect coupler. The end fitting of the securing means comprises three cylindrical portions 44, 46, and 48. Moving from the upstream terminus of the end fitting to the central portion of the sample delivery module 40, the diameter of each cylindrical portion is successively larger. The outermost terminal cylindrical portion 44 itself terminates in a frustoconical segment 50.

Between the terminal cylindrical portion 44 and the central cylindrical portion 46, a second frustoconical segment 52 provides a gradual transition from the diameter of the first cylindrical portion 44 to that of the second cylindrical portion 46. Between the second cylindrical portion 46 and the third cylindrical portion 48, no such gradual transition is provided. Thus, there is an abrupt increase in diameter of the preferred embodiment from the second cylindrical portion 46 to the third cylindrical portion 48. The third cylindrical portion 48 provides a convenient hand-hold for an operator, and facilitates engagement of the sample delivery module into the connector 37.

A number of other quick-locking types of couplers may be used in the practice of the invention. It is particularly intended, for example, that a "luer-lok" fitting, of the type used on syringes, can be substituted for the securing means depicted in the illustrated embodiment of FIG. 4.

It is also preferable that the securing means 42 be positively engagable with the connector 37. For example, an annular groove 54 can be provided on the outer surface of the second cylindrical portion 46. The groove can be adapted in size and shape to be positively engaged by a detent provided by the connector 37. In this regard, a plurality of balls (e.g., of the type found in a ball bearing) can be provided as a detent means in the connector 37. The balls and the annular groove 54 are positioned such that, upon tightening of the connector 37, the balls are seated within the annular groove 54, where they remain until the connector 37 is decoupled.

A linking portion 56 is arranged adjacent to the end fitting 42. The linking portion 56 preferably has a cylindrical geometry, and in one embodiment, has a smaller diameter than that of the third cylindrical portion 48 of the securing means 42. In this way, the third cylindrical portion 48 is accessible during installation of the sample delivery module 40. A conical exit nozzle 58 is arranged at the opposite end of the linking portion 48. The exit nozzle 58 is configured as described herein above. In this regard, the diameter of the conical exit nozzle 58 is preferably narrower near the linking portion 56 than at its opposite end. The particular dimensions and conical angle of the exit nozzle 58 will depend upon the input gas pressure of the instrument.

Optionally, spacer legs 60 can be connected to the wider, downstream terminus of the exit nozzle 58. The spacer legs 60 are generally selected to have a length suitable for delivery of particles to a desired target. Such spacer legs 60 are not required, but are advantageous because they allow an operator to establish a suitable distance between the instrument 10 and the target. This allows for reproducible results between subsequent particle deliveries. The proper distance may be determined and fixed as needed by varying the length of the spacer legs 60, using empirical observations of the appearance of target cells and measured levels of gene expression after delivery. It has been found for mammalian skin that a spacer leg length of ¾ to 1 inch is preferable. Alternatively, it is possible to manually position the instrument at a desired distance from the target. Usually at least one, and preferably two or more spacer legs 60 are provided. The spacer legs of one particular embodiment are best viewed in FIGS. 5–7. If desired, the sample delivery module can be provided in a sealed, sterile container 70 of a type commonly used to store single-use medical device parts.

A hollow channel is provided along the entire length of the sample delivery module 40. This hollow channel provides a sample path that is substantially coaxial with the major axis of the sample delivery module 40. Referring to the sectional view of FIG. 5, the sample path includes a cartridge chamber 62 that is axially disposed within the securing means 42 and extends from the upstream terminus of the securing means, through the first cylindrical portion 44, and into the second cylindrical portion 46. The cartridge chamber 62 admits an accelerated gas stream from the motive force-generating portion of the instrument 10. The cartridge chamber 62 is configured to accept and retain a particle cartridge (described below) having carrier particles removably secured to an interior concave surface thereof. The diameter of the cartridge chamber 62 is narrower at its downstream terminus relative to its upstream terminus. This restricts movement of a particle cartridge when retained within the cartridge chamber.

The narrowed terminus of the cartridge chamber 62 is in fluid communication with the upstream terminus of a substantially linear, particle acceleration passage 64 having a diameter that is smaller relative to that of the cartridge chamber 62. The relative diameters of the cartridge chamber 62 and the particle acceleration passage 64 can be seen by reference to FIGS. 5 and 6. The particle acceleration passage 64 is arranged substantially coaxially with the major axes of the sample delivery module 40 and the cartridge chamber 62. The passage 64 in one embodiment can have a diameter of 1/16 of an inch, and a length of 5 to 15 mm. If the passage 64 is too long, the gas stream may lose momentum due to friction. The particle acceleration passage 64 extends between the downstream terminus of the cartridge chamber, and the upstream terminus of the conical exit nozzle 58.

Figures 5, 7:
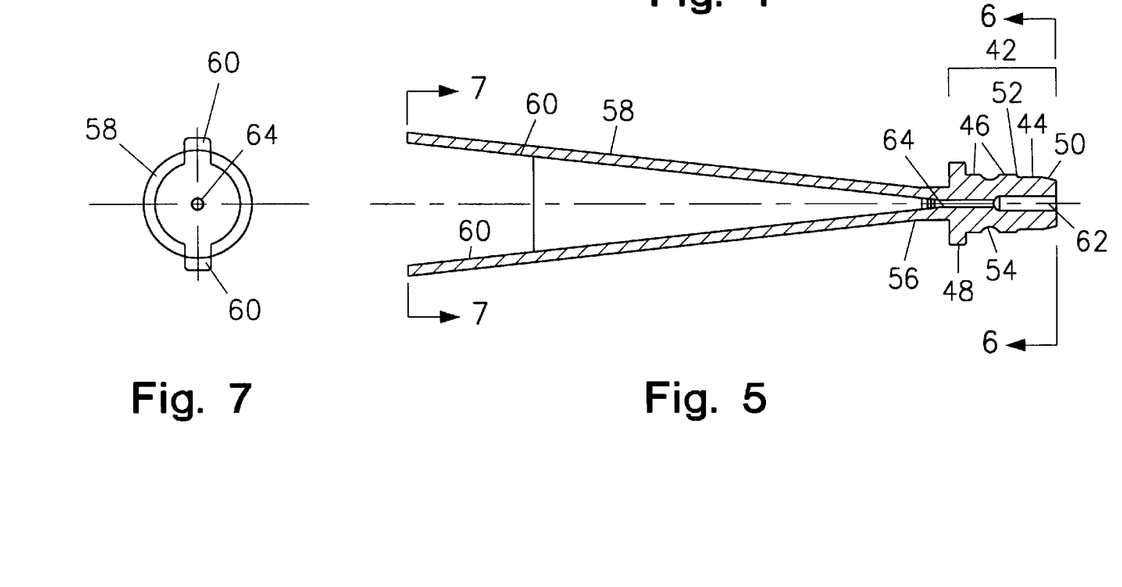
FIG. 5 is a side sectional view taken along line 5—5 of FIG. 4.
FIGS. 6 and 7 are end views of the embodiment of FIG. 4.
Figure 6:
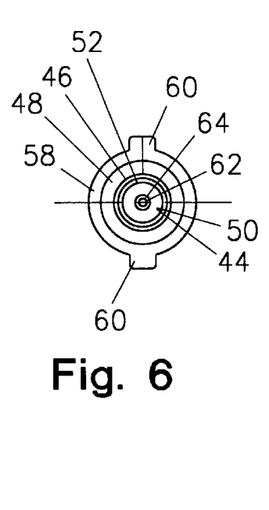

Maintaining a smooth interior surface for the acceleration passage 64 reduces any drag or adverse interaction between the carrier particles and the passage 64, thus facilitating a proper flow of the carrier particles toward the intended target. To maintain such a smooth surface, a string or pipe cleaner can be coated with a polishing compound and then used to polish the interior of the passage 64. A suitably smooth interior surface for the passage can also be formed directly in a molding process if the sample delivery module is formed from a thermoplastic material. The exit nozzle 58 also preferably has a smooth interior surface.

In use, a sample cartridge, is inserted into the cartridge chamber 62 such that its interior surface, which has carrier particles attached thereto, is in fluid communication with the gas stream when the sample delivery module 40 is installed. Orientation of the particles within the sample cartridge is otherwise not critical. The sample delivery module 40 is coupled to the connector 37 by way of the securing means 42, thereby preventing unintentional separation of the sample delivery module 40 from the instrument 10 during use. The trigger mechanism 30 that controls the gas flow actuator 34 is actuated to release compressed gas from tube 32. The released gas flows in a stream from the actuator 34 toward the sample delivery module 40, passing through the sample cartridge and releasing and carrying away particles from the surface thereof. The gas stream, and the carrier particles entrained therein, pass through the particle acceleration passage 64, into the conical nozzle 58 and toward and into a target.

As described above, precise operating parameters depend generally on the gas pressure being used to deliver the carrier particles which, in turn, dictates the particular dimensions of the particle acceleration passage 64 and exit nozzle 58.

After a sample of coated particles has been delivered from the apparatus 10, the connector 37 is released to remove the sample delivery module 40. In preferred embodiments wherein the module is intended for single use, the spent module can be suitably disposed of. Subsequent deliveries can then be carried out by repeating the above-described steps using a new sample cartridge and sample delivery module 40.

The present invention is particularly useful for delivery of biological materials since all portions of the particle acceleration apparatus that actually contact the sample and a target surface are provided separately from the motive force portion of the instrument, and can be readily disposed of after a single use. Thus, the potential for cross-contamination with residual biological materials from previous deliveries is effectively eliminated. Routine disposal of spent sample delivery modules also prevents any cross-contamination between or among recipients, since no portion of the instrument that comes into contact with a recipient needs to be reused.

The present invention can be used in mass vaccination of mammalian subjects, such as rodents, cattle, pigs, sheep, goats, horses and man, and domestic animals such as dogs and cats, using nucleic acid vaccines. Nucleic acid vaccines comprise genetic material, usually DNA, derived from a pathogenic agent. The genetic material is delivered into cells of a mammalian subject using a device such as those described herein. Once delivered into a cell, the genetic material is expressed by the cellular transcription and translation machinery to produce a protein or peptide which engenders an immune response in the vaccinated subject. The immune response can render the vaccinated subject resistant to subsequent infection by the agent from which the vaccine was derived, or provide a therapeutic effect in an already infected subject. The apparatus described herein may also be used for gene delivery, such as gene therapies.

While the present invention has been specially designed for use in large scale, repetitive delivery of biological materials, it can also be used for more traditional applications, such as with existing particle acceleration devices for single, discrete delivery of carrier particles into a target surface. For example, the sample delivery module, and a particle acceleration apparatus employing the subject module, can be used in methods for transferring genetic material into organs, tissues, and/or cultured cells of plants and animals. The present invention has been used with a particle acceleration apparatus to deliver genes into the meristems of living plants to create transgenic plants. All of the advantages of the invention, particularly its portability and ease of sample handling, apply equally well when the apparatus is used for one-shot delivery of a gene by particle acceleration. However, the principle of the invention may also be incorporated into a stationary non-portable unit to achieve substantial advantages in speed, reproducibility and ease of use.

Accordingly, novel sample delivery modules for use with a particle acceleration apparatus have been described. Although preferred embodiments of the subject invention have been described in some detail, it is understood that obvious variations can be made without departing from the spirit and the scope of the invention as defined by the appended claims.

We claim:

1. A sample delivery module for use in a particle acceleration apparatus, said module comprising:
   (a) a cartridge chamber configured to accept and retain a particle cartridge, said chamber having an upstream terminus and a downstream terminus;
   (b) an exit nozzle having an upstream terminus and a downstream terminus;

(c) a particle acceleration passage arranged between the cartridge chamber and the exit nozzle, wherein said acceleration passage is in fluid communication with the downstream terminus of the cartridge chamber and the upstream terminus of the exit nozzle; and (d) securing means for coupling the sample delivery module to a source of motive force, wherein said securing means interfaces the upstream terminus of the cartridge chamber with an associated source of motive force.

2. The sample delivery module of claim 1, wherein the exit nozzle is conical.

3. The sample delivery module of claim 2, wherein the downstream terminus of the exit nozzle has a greater diameter than the upstream terminus thereof, and further wherein the distance between the upstream and downstream termini of the exit nozzle is greater than the diameter of the downstream terminus.

4. The sample delivery module of claim 1 further comprising a plurality of spacer legs extending from the downstream terminus of the exit nozzle.

5. The sample delivery module of claim 1, wherein said module is comprised of a polymeric material.

6. The sample delivery module of claim 5, wherein said polymeric material is a thermoplastic resin.

7. The sample delivery module of claim 6, wherein the module is intended for a single particle delivery operation.

8. The sample delivery module of claim 5, wherein said polymeric material is a polycarbonate or polypropylene.

9. The sample delivery module of claim 8, wherein the module is intended for multiple particle delivery operations.

10. A sterile, sealed container comprising the sample delivery module of claim 1.

11. The sample delivery module of claim 1, wherein the securing means provides a positive, pressure-tight coupling between the module and an associated source of motive force.

12. The sample delivery module of claim 11, wherein the securing means is adapted to cooperate with a quick-connect fitting on an associated source of motive force.

13. The sample delivery module of claim 12, wherein said securing means comprises an annular groove for cooperating with a detent coupler on an associated source of motive force.

14. The sample delivery module of claim 1 further comprising a concave sample cartridge containing carrier particles coated with a biological material.

15. The sample delivery module of claim 14, wherein the sample cartridge is tubular.

16. The sample delivery module of claim 15, wherein the acceleration passage has a smaller diameter than that of the tubular sample cartridge.

17. A particle acceleration apparatus comprising the sample delivery module of claim 1.

* * * * *